(12) United States Patent
McNall, III et al.

(10) Patent No.: US 10,406,279 B2
(45) Date of Patent: Sep. 10, 2019

(54) UNIFIED DRUG MIXER AND DISPENSER

(71) Applicant: BioQ Pharma Incorporated, San Francisco, CA (US)

(72) Inventors: Ralph I. McNall, III, Belmont, CA (US); Thomas T. Donze, San Bruno, CA (US); Andrew M. MacDonell, San Francisco, CA (US)

(*) Notice: Subject to any disclaimer, the term of this patent is extended or adjusted under 35 U.S.C. 154(b) by 0 days.

(21) Appl. No.: 15/958,941

(22) Filed: Apr. 20, 2018

(65) Prior Publication Data

US 2018/0236162 A1  Aug. 23, 2018

Related U.S. Application Data

(63) Continuation of application No. 15/687,393, filed on Aug. 25, 2017, which is a continuation of application
(Continued)

(51) Int. Cl.
*A61M 5/14* (2006.01)
*A61J 1/20* (2006.01)
(Continued)

(52) U.S. Cl.
CPC .............. *A61M 5/1407* (2013.01); *A61J 1/20* (2013.01); *A61J 1/202* (2015.05); *A61J 1/2093* (2013.01); *A61M 5/142* (2013.01); *A61M 5/1408* (2013.01); *A61M 5/1409* (2013.01); *A61M 5/1413* (2013.01); *A61M 5/14232* (2013.01); *A61M 5/16827* (2013.01); *A61M 5/16881* (2013.01); *B65D 55/06* (2013.01); *B65D 55/066* (2013.01); *A61M 5/14244* (2013.01); *A61M 2205/8206* (2013.01)

(58) Field of Classification Search
CPC ............ A61J 1/2093; A61J 1/20; A61J 1/202; A61M 5/1408; A61M 5/1407; A61M 5/1409; A61M 5/1413; B65D 25/04; B65D 25/08; B65D 55/06; B65D 55/066
USPC ..................................................... 604/82–86
See application file for complete search history.

(56) References Cited

U.S. PATENT DOCUMENTS 9,775,946 B2 * 10/2017 McNall, III ............ A61J 1/202
2014/0318995 A1 * 10/2014 Eilertsen ............... A61J 1/2096
206/219

FOREIGN PATENT DOCUMENTS

WO        2010082966 A1    7/2010

* cited by examiner

Primary Examiner — Nathan R Price
Assistant Examiner — Anh Bui
(74) Attorney, Agent, or Firm — Thomas W. Galvani, P.C.; Thomas W. Galvani

(57) ABSTRACT

A unified dispenser for holding, mixing, and dispensing a drug includes a housing holding a diluent reservoir, a drug reservoir, and a tubing set connecting and defining a fluid communication path therebetween. A first occlusion is at the diluent reservoir, and a second occlusion is at the drug reservoir. In a storage state of the dispenser, the first and second occlusions are entirely encased within the housing and occlude the fluid communication path. First and second pull assemblies extend outside the housing. The first and second pull assemblies are coupled to the first and second occlusions, respectively, so that removal of the first and second pull assemblies removes the first and second occlusions and joins the diluent reservoir to the drug reservoir in fluid communication through the tubing set, thereby arranging the dispenser from the storage state to a use state.

25 Claims, 7 Drawing Sheets

Related U.S. Application Data

No. 15/041,157, filed on Feb. 11, 2016, now Pat. No. 9,775,946.

(51) Int. Cl.
*A61M 5/142* (2006.01)
*A61M 5/168* (2006.01)
*B65D 55/06* (2006.01)

UNIFIED DRUG MIXER AND DISPENSER

CROSS-REFERENCE TO RELATED APPLICATIONS

This application is a continuation of and claims the benefit of U.S. patent application Ser. No. 15/687,393, filed Aug. 25, 2017, which is a continuation of and claims the benefit of prior U.S. patent application Ser. No. 15/041,157, filed Feb. 11, 2016, all of which are hereby incorporated by reference.

FIELD OF THE INVENTION

The present invention relates generally to medical equipment, and more particularly to devices for mixing and dispensing drugs to a patient.

BACKGROUND OF THE INVENTION

Precise infusion of large volumes of liquid medicament through an administration line is usually accomplished by an infusion pump. Traditional infusion pumps make use of a flexible infusion bag suspended above the patient. For many medicaments and drugs, a pharmacist, nurse, doctor, or other medical professional is required to prepare the infusion bag by reconstituting, diluting, or mixing the medicament or drug in preparation for its delivery and use with a pump. Such methods are cumbersome, imprecise, require many time-consuming steps by medical professionals, are susceptible to medication errors, and require bed confinement of the patient. Mixing and administration of solid state drugs— whether lyophilized powders, crystalline structures, or some other solid state—and solution state drugs is time consuming and involves a large number of complicated steps.

Other problems exist with conventional pumps. Periodic monitoring of the apparatus by a nurse, doctor, or other medical professional is required to detect malfunctions of the infusion pump. Accordingly, over the years, infusion pumps developed into increasingly more complex devices of great expense and sophistication. Such devices include a large number of features, options, and programmability possibilities. While those capabilities can be advantageous in providing a range of customization to medicament administration, they also lead to use error, and the possibility of patient harm, injury, or death.

Complicated infusion pumps also typically require many time-consuming steps for setup, including applying both the medicament reservoir and the administration line to the pump. Increased preparation requirements increase the risk of contaminating the pump, the medicament reservoir, the administration line, or other elements of the intravenous line system, posing a hazard to the patient. With mixed drug administration systems (such as reconstituted or diluted drug administration systems), there is also an increased risk that the drug or diluent into which the drug is diluted will be contaminated, mis-measured, or otherwise incorrectly prepared, leading to patient harm. An improved system for providing a convenient, reliable, accurate, and sterile infusion of large volumes of mixed drugs is needed.

SUMMARY OF THE INVENTION

A unified drug mixer and dispenser is described herein. The dispenser holds, mixes, and dispenses a drug to a patient with a dramatically lower risk of contamination or improper operation, thereby providing a more reliable, consistent, and safe patient experience. The dispenser is unified in that all components are encased and sterile—either aseptically or through a sterilization process—and do not require the assembly, preparation, and set up conventionally required by prior art dispensers that can lead to patient harm. Rather, the dispenser includes a housing holding a diluent reservoir, a drug reservoir, and a tubing set connecting the two reservoirs and defining a sterile fluid communication path together with them. Occlusions occlude this sterile pathway: a first occlusion is located at the diluent reservoir, and a second occlusion is located at the drug reservoir. The occlusions are encased entirely within the housing, but pull assemblies, which extend from the occlusions to outside the housing, provide the medical professional with a way to remove those occlusions without invading the sterile communication path. By removing the pull assemblies, a medical professional both opens the fluid communication path so that fluid may flow through it, and energizes the device for operation.

BRIEF DESCRIPTION OF THE DRAWINGS

Referring to the drawings.

DETAILED DESCRIPTION

Figure 1:
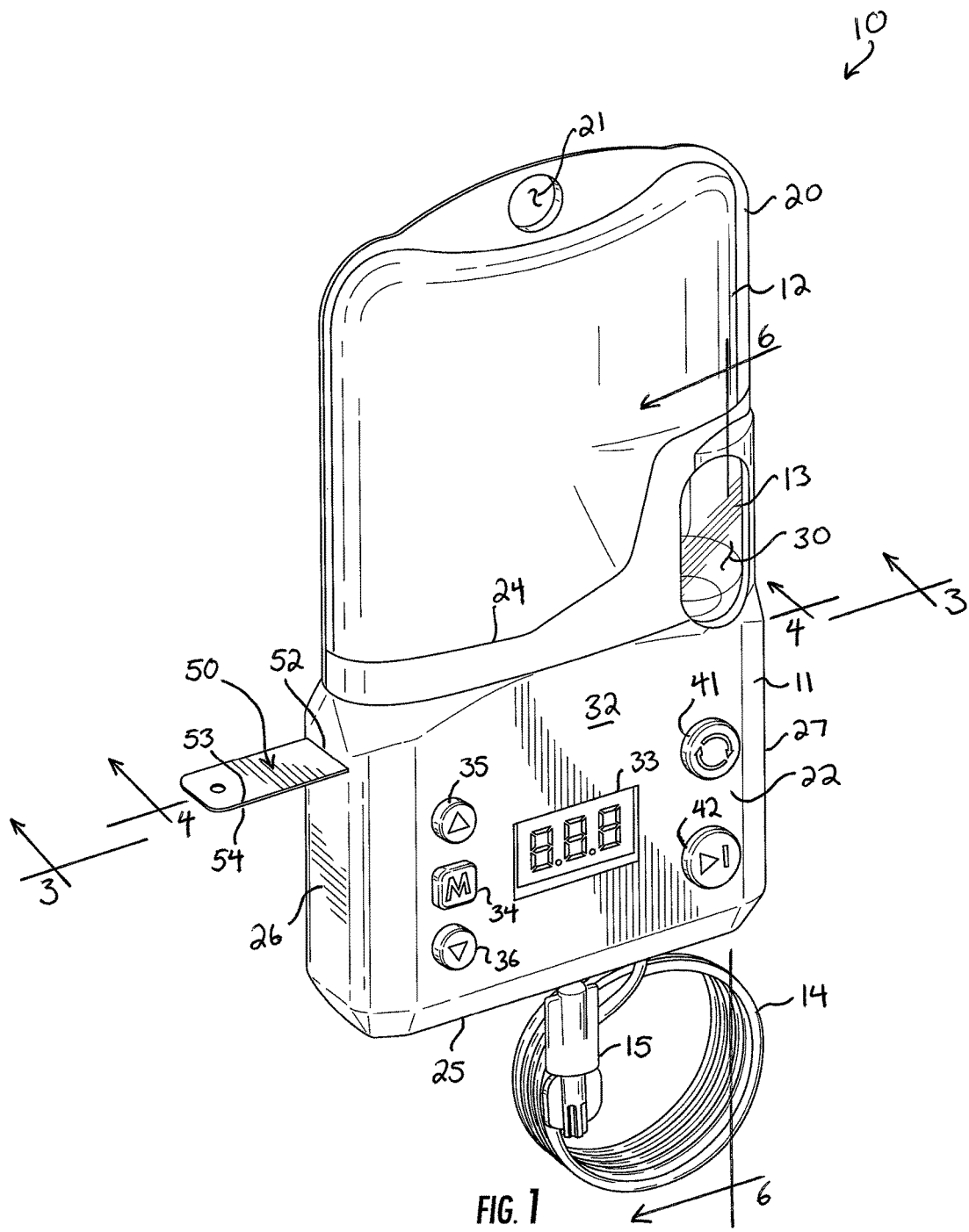
FIGS. 1 and 2 are front and rear perspective views illustrating the housing of a unified drug mixer and dispenser.
Figure 2:
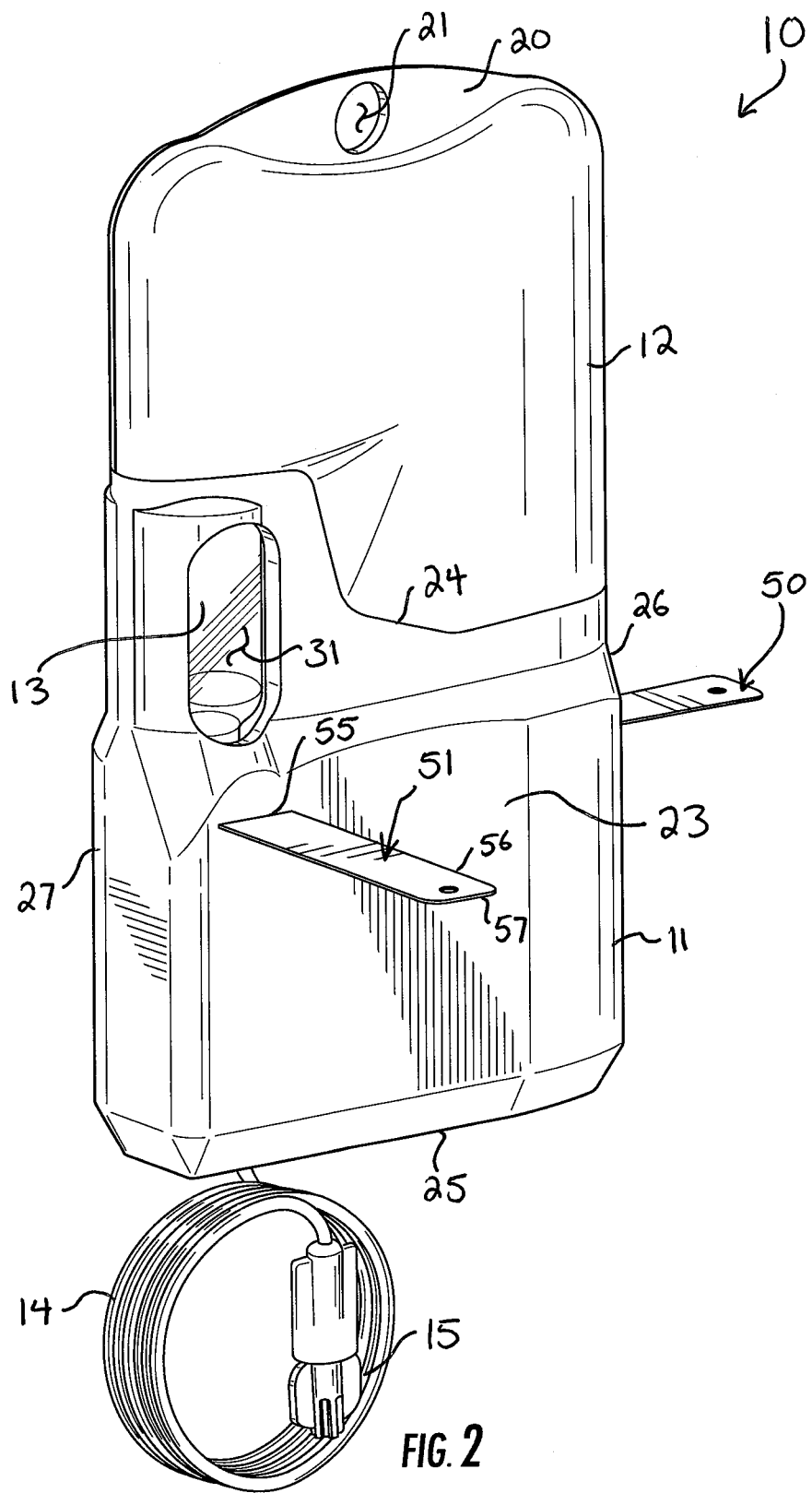

Reference now is made to the drawings, in which the same reference characters are used throughout the different figures to designate the same elements. FIGS. 1 and 2 illustrate front and rear perspective views of a unified drug mixer and dispenser 10 useful for holding, mixing, and delivering a large quantity of medicament to a patient via an administration line at a controlled rate set according to several parameters. The dispenser 10 includes a housing 11 containing a diluent reservoir 12 and a drug reservoir 13. The dispenser 10 is a "ready-to-use" dispenser 10 in that it uniquely contains both a drug and a diluent, in disparate sterile reservoirs within a single unit, and that it mixes and dispenses the drug to a patient through sterile pathways without the need for separate mixing or preparation which could expose the drug or the components of the dispenser to contamination. The drug in the drug reservoir 13 is in a concentrated form, either in a solid state or solution state. For example, solid state drugs include powdered, lyophilized powdered, crystallized, dried, and other solid state forms. Drugs in a solution state are emulsions, aqueous solutions, or other liquid preparations wherein the drug is dissolved, dispersed, suspended, or otherwise carried in a solvent or liquid. Because the diluent reservoir 12 and the drug reservoir 13 contain and hold the drug separately from the diluent, and because, as will be explained, the dispenser 10 reconstitutes, mixes, or dilutes the drug by communicating diluent into the drug reservoir, the structure and function of the dispenser 10 does not change depending on whether the drug reservoir contains a solid state or solution state drug. As such, one having ordinary skill in the art will understand that the following description applies equally to a dispenser 10 for holding, reconstituting, and dispensing a solid state drug as it does for holding, diluting, and dispensing a solution state drug. Therefore, throughout this description, the word "reconstitute," and variations thereof, is used primarily when referring to solid state drugs, and the words "mix" and "dilute," and variations thereof, are used primarily when referring to solution state drugs, but all three of the terms may also be used alone when referring to both solid state and solution state drugs, without exclusion of one or the other. Indeed, the term "mix" will be used most generally and is meant to include "reconstitute" and "dilute."

The diluent reservoir 12 and drug reservoir 13 are both coupled to each other and to a pump to mix the diluent and the drug in a solid or solution state into a mixture, and to then communicate that mixture through an administration line 14 to a capped coupling 15. This coupling 15 then conventionally interfaces with an intravenous line for application to a patient. The dispenser 10 is preferably a unified, single-use, disposable dispenser with a sterile, pre-filled diluent, a sterile, prefilled drug, and which is ready for use without the need for disassociated preparation, assembly, or complicated programming. The dispenser 10 thus helps prevent user error, infection, injury, and even death.

The housing 11 is generally rectangular prismatic and constructed from a durable, rigid plastic, either in a monolithic construction or formed from several pieces coupled together by snap tab fittings, adhesive, sonic welding, screws, or like fastening methods suitable for an assembled enclosure. The embodiment shown throughout these drawings is a preferred, yet not limiting embodiment, and it should be understood that variations in the design of various structural elements—such as the housing 11—do not alter the principle operation of the dispenser 10. The diluent reservoir 12, described in detail below, is seated into the housing 11 and is preferably a flexible, collapsible container or bag including a semi-rigid perimeter edge 20 to provide the reservoir 12 with some degree of rigidity. A hole 21 is formed through the top of the edge 20 so that the dispenser 10 can be hung from a stand. For purposes of clarity of the description, the terms "vertical" and "horizontal" will be used herein to describe various structures and orientations of structures. "Vertical" is used herein to indicate an orientation generally parallel to a line running from the top of FIG. 1 to the bottom of FIG. 1, and "horizontal" is used herein to indicate an orientation generally perpendicular to vertical. The hole 21 allows the dispenser 10 to hang in a vertical orientation. For this reason, and for purposes of orientation, the relative location of structural elements and features may be described in terms of "above" or "upward" and "below" or "downward."

Referring still to FIGS. 1 and 2, the housing 11 has a thin-wall construction and includes a front 22, back 23, top 24, and bottom 25. The housing 11 includes opposed sides 26 and 27, which are referred to herein as a left side 26 and a right side 27. A window 30 is formed in the front 22 of the housing 11 and an opposed window 31 is formed in the back 23 of the housing 11. The windows 30 and 31 correspond to each other in size and shape, are oval-shaped, and frame the drug reservoir 13 proximate to the top 24 and the right side 27 of the housing 11. The windows 30 and 31 are preferably, though not necessarily, each open, having no covering, film, or other barrier disposed thereacross. Each of the windows 30 and 31 has parallel sides and a curved top and curved bottom. The windows 30 and 31 provide a person with the unique ability to view and observe the drug in the drug reservoir 13. The opposed windows 30 and 31 also uniquely allows the drug reservoir 13 to be backlit with any of a variety of illumination techniques for visual and other analysis.

Figure 6:
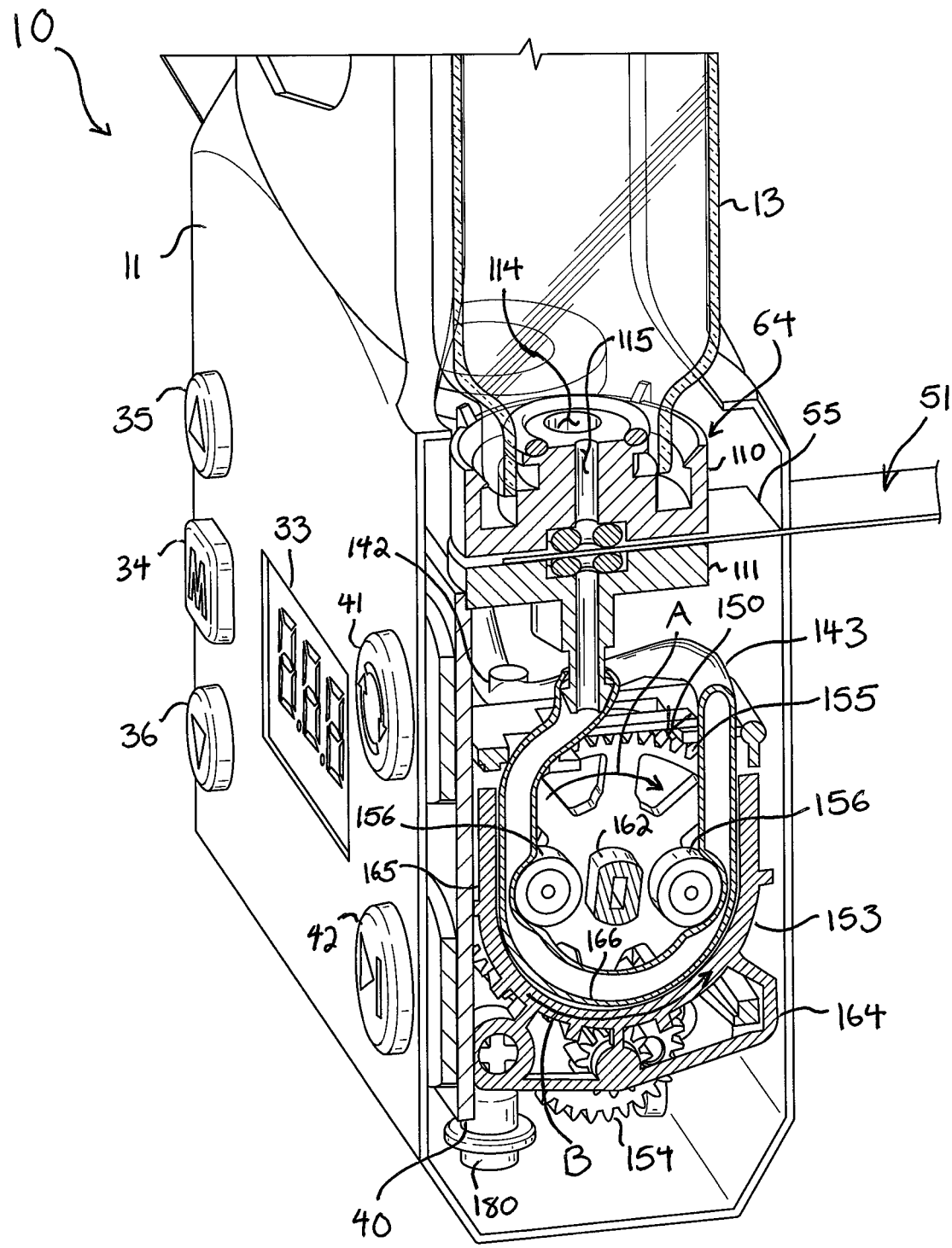
FIG. 6 is a section view of the unified drug mixer and dispenser of FIG. 1 taken along the line 6-6 in FIG. 1.

The front 22 of the housing 10 has a wide, flat face 32 into which is set a plurality of control buttons and a display 33. On the face 32, proximate to the left side 26, a setting button 34 and two navigation buttons 35 and 36 are set into and extend through the housing 11. The buttons 34, 35, and 36 are carried on and operatively coupled to a printed circuit board 40 (hereinafter, "PCB 40") within the housing 11, as shown in FIG. 6. The display 33 is also carried on the PCB 40 and set into and through the face 32, in a window in the housing 11 sized and shaped to exactly correspond to the display 32. Depressing the setting and navigation buttons 34, 35, and 36 controls operation of the dispenser, as is described later. Proximate to the right side 27, a mix button 41 and a dispense button 42 are set into and extend through the housing 11. The mix and dispense buttons 41 and 42 are also carried on and operatively coupled to the PCB 40. The setting and navigation buttons 34, 35, and 36 are aligned vertically with each other, and the opposed mix and dispense buttons 41 and 42 are aligned vertically with each other. The display 33 is roughly centered between the two sets of buttons, and between the sides 26 and 27.

Figure 3:
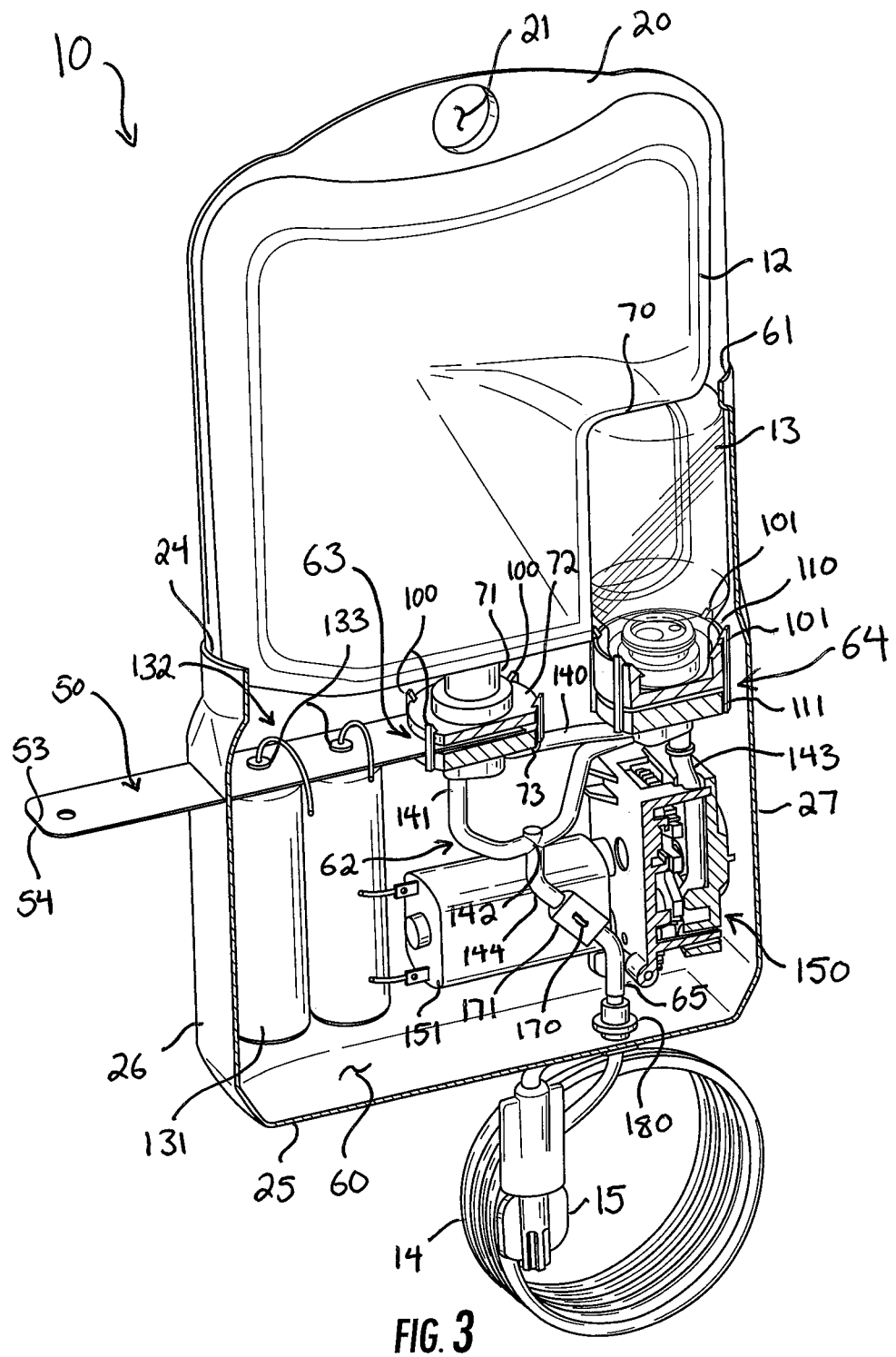
FIG. 3 is a section view of the unified drug mixer and dispenser of FIG. 1 taken along the line 3-3 in FIG. 1.

Two pull assemblies 50 and 51, or more simply, pulls 50 and 51, in the dispenser 10 maintain sterility throughout the dispenser 10 and control activation and energization of the dispenser 10. Turning to FIG. 1 only, a side pull 50 extends through a narrow slit 52 formed through the left side 26 of the housing 11. The side pull 50 is a two-ply ribbon consisting of a wide upper ribbon 53 and a coextensive wide lower ribbon 54. The ribbons 53 and 54 are mechanically and electrically coupled to arrange and configure the dispenser 10 from a storage state to an operation or use state, as is explained in detail later. The ribbons 53 and 54 each have anchored ends within the housing 11, as seen in FIG. 3, and as is explained below. The ribbons 53 and 54 are preferably secured to each other, such as at their free ends, which extend out of the housing 11 so that the ribbons 53 and 54 of the pull 50 are grasped and pulled simultaneously. Now turning to FIG. 2, a rear pull 51 is shown as extending through a narrow slit 55 in the back 23 of the housing 11. The rear pull 51 is also a two-ply ribbon having a wide upper ribbon 56 and a coextensive wide lower ribbon 57, which are mechanically and electrically coupled to arrange and configure the dispenser 10 from the storage state to the use state. The ribbons 56 and 57 each have anchored ends within the housing 11, as seen in FIG. 3. The ribbons 56 and 57 are preferably secured to each other, such as at their free ends, which extend out of the housing 11 so that the ribbons 56 and 57 of the pull 51 are grasped and pulled simultaneously.

Turning now to FIG. 3, which is a section view taken along the line 3-3 in FIG. 1, an interior 60 of the dispenser 10 is shown along with the various components encased within the housing 11. The interior 60 is a single compartment defined between the front 22, back 23, top 24, bottom 25, and opposed sides 26 and 27. As can be seen most clearly in FIG. 3, the top 24 of the housing 11 itself includes an open mouth 61, into which the diluent reservoir 12 is seated. The diluent reservoir 12 is seated continuously against the open mouth 61. While the seal formed by this seating does not need to maintain sterility of the interior 60, it does provide a seal against intrusion of dust and debris, and thus protects the various structural elements and features carried within the interior 60 from damage.

A sterile fluid communication path 62 is carried by the dispenser 10 to deliver a drug to a patient. The fluid communication path 62 uniquely provides a sterilized, assembled, transported, stored, connected, and set up system for delivering the drug to a patient safely and without compromising sterility. The fluid communication path 62 includes the diluent reservoir 12, the drug reservoir 13, a diluent aseptic connector assembly 63 (hereinafter, the "DACA 63"), a drug aseptic connector assembly (hereinafter, the "LACA 64"), a tubing set 65, and the administration line 14. The fluid communication path 62 is a sterile pathway for delivering the reconstituted, mixed, or diluted drug to a patient and maintains a sterile pathway during the lifecycle of the dispenser 10. The internal surfaces of each of the components of the fluid communication path 62, namely, the diluent reservoir 12, the drug reservoir 13, the DACA 63, the LACA 64, the tubing set 65, and the administration line 14 are sterilized prior to assembly, and the dispenser 10 is assembled carefully to maintain the sterility of the fluid communication path 62, so that the dispenser 10 reliably provides a safe drug to the patient. Preferably, and as described in more detail below, the diluent reservoir 12 together with a portion of the DACA 63, is sterilized separately from the drug reservoir 13 together with a portion of the LACA 64, which is sterilized separately from the tubing set 65 and administration line 14 and complemental portions of the diluent and drug aseptic connectors 63 and 64. The fluid communication path 62 is then assembled into the housing 11 with the other structural elements and features carried by the housing 11 which interact with the fluid communication path 62 to store, power, operate, and control the dispenser 10.

The diluent reservoir 12 has been discussed briefly above. With reference still to FIG. 3, the diluent reservoir 12 extends entirely between the left and right sides 26 and 27. The diluent reservoir 12 is generally rectangular prismatic in shape but for a notched corner 70. The corner 70—an inside corner—is notched inwardly into the diluent reservoir 12 to form a recess into which the drug reservoir 13 is disposed when applied to the housing 11, accommodating the drug reservoir 13 against the housing 11. The diluent reservoir 12 is a pre-filled, flexible, collapsible container or bag. "Pre-filled" is used here to mean that the diluent fluid is applied to the diluent reservoir 12 before assembly of the diluent reservoir 12 into the housing 11 and before the diluent reservoir 12 is coupled to any other structural element or feature of the dispenser 10. Further, the diluent reservoir 12, together with a portion of the DACA 63, is sterilized before assembly into the housing 11 and before coupling to the other structural elements and features of the dispenser 10. The diluent reservoir 12 is transparent or at least translucent so that a user can observe the diluent therein and the mixing of the drug in the diluent reservoir 12. In some embodiments, the diluent reservoir 12 is contained within a transparent, rigid encasing surrounding the diluent reservoir 12 and providing means, similar to the rigid edge 20 and the hole 21 formed therein, for hanging the dispenser 10 from a stand. In some embodiments, the diluent reservoir 12 includes graduated volume indication lines to indicate the volume of liquid in the diluent reservoir 12. The diluent reservoir 12 preferably can hold between approximately 50 and 500 milliliters of diluent. The type of diluent itself will be determined on a case-by-case for each patient by prescription, but will typically be either Water-for-Injection, 5% dextrose, 0.9% sodium chloride, Lactated Ringer's Injection, Normosol®-M, ISOLYTE® E, or a combination of these compounds. The diluent is not shown in the drawings, as one having ordinary skill in the art will readily appreciate its existence and flow through the dispenser 10. The diluent reservoir 12 is fluid impermeable, constructed from a material or combination of materials having characteristics of inertness, low permeability, durability, flexibility, and collapsibility, such as PVC, polypropylene, HDPE, COC, or COP. The diluent reservoir 12 includes a spout 71 terminating in an upper diluent aseptic connector 72 (hereinafter, "UDAC 72") which is mated against a lower diluent aseptic connector 73 (hereinafter, "LDAC 73") to form the DACA 63. The spout 71 is preferably sonically welded to the UDAC 72 to permanently couple those components.

Figure 4:
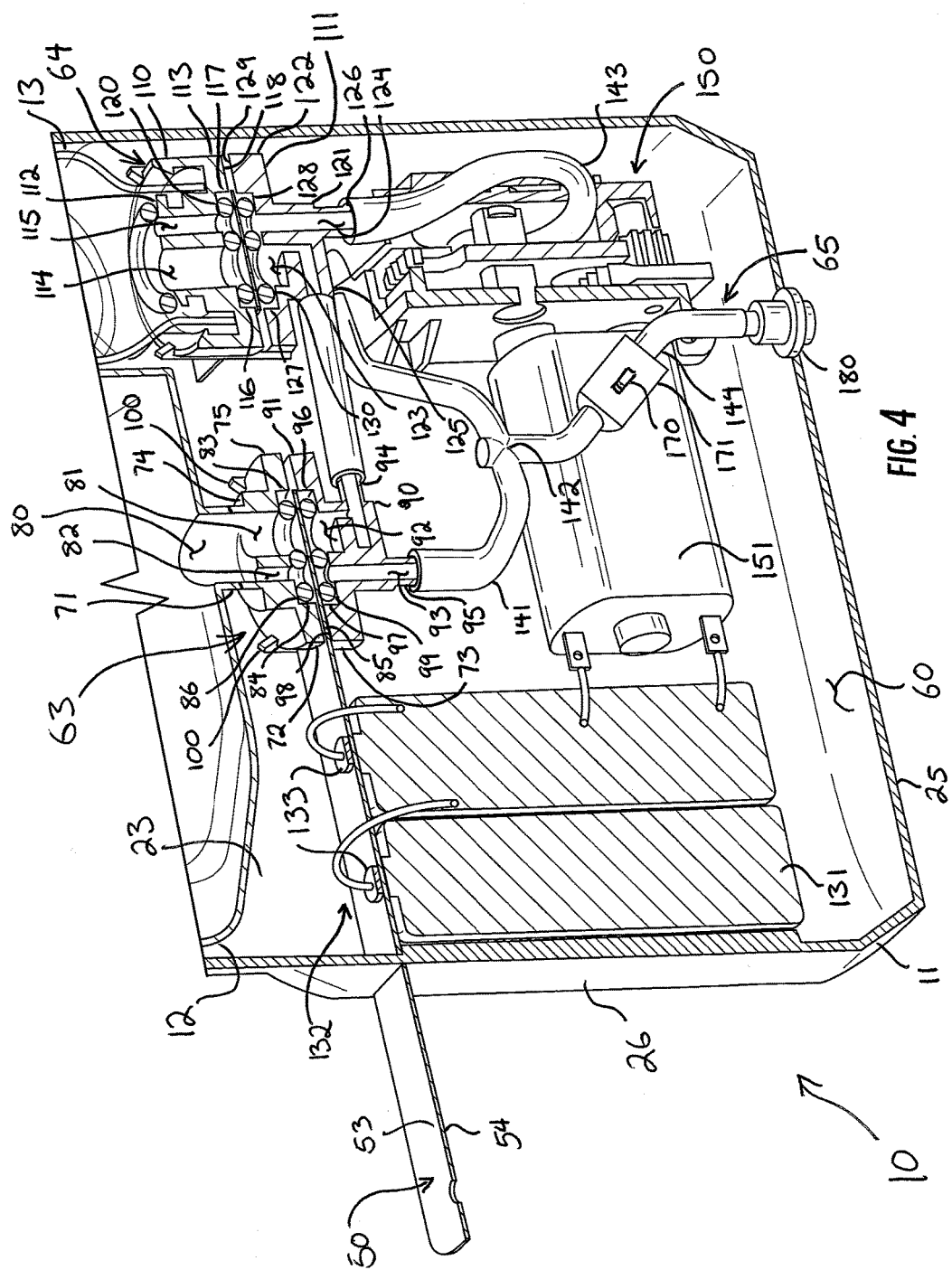
FIG. 4 is an enlarged section view taken along the line 4-4 in FIG. 1, showing in detail a tubing set and pump assembly of the unified drug mixer and dispenser of FIG. 1.

The DACA 63 is shown in greater detail in FIG. 4. The UDAC 72 and LDAC 73 are mated to each other in compression to form a single, leak-proof assembly. The UDAC 72 includes a short post 74 and a wide, circular base 75 depending coaxially therefrom. A single open throat 80 in the spout 71 of the diluent reservoir 12 transitions into and thus communicates with both a major bore 81 and a minor bore 82 extending through the post 74 and the base 75. The minor bore 82 has a diameter approximately one-third the diameter of the major bore 81. Both of the major and minor bores 81 and 82 provide a pathway for movement of fluid through the UDAC 72, so that fluid flows both into and out of both of the major and minor bores 81 and 82 depending on the selected mix or dispense function of the dispenser 10.

Two cylindrical seats are formed into a face 85 of the base 75 opposite the post 74: a major seat 83 coaxial to and communicating with the major bore 81, and a minor seat 84 coaxial to and communicating with the minor bore 82. A single gasket 86 is fit into both of the major and minor seats 83 and 84. The gasket 86 has a figure-eight shape with a large annulus and a small annulus and two holes, formed coaxially though the large and small annuli. The gasket 86 has a height just slightly greater than the depth of the major and minor seats 84 and 85, so that the gasket 86 protrudes slightly beyond the face 85 of the base 75. The gasket 86 is constructed from a material or combination of materials having characteristics of inertness, low permeability, durability, and compressibility, such as rubber. The upper ribbon 53 is applied over the gasket 86, is adhered to the face 85 of the UDAC 72 with a peelable bond, and is thereby sealed to the face 85 of the UDAC 72. The upper ribbon 53 completely overlies the gasket 86 with a continuous, annular seal formed between the upper ribbon 53 and the face 85 to act as a barrier to fluid migration.

The LDAC 73 is somewhat similar to the UDAC 72, though deserves its own description for explanation of its differences. The LDAC 73 includes a post 90 and a wide, circular base 91 extending coaxially therefrom. A major bore 92 extends vertically through the base 90 and turns laterally, reducing in diameter in the post 91 before extending horizontally out of the post 91 as a barbed coupling 94. A minor bore 93 extends vertically through both the base 90 and the post 91 and terminates as a barbed coupling 95 pointing down. The major and minor bores 92 and 93 are entirely separated by an internal wall in the post 90 and the base 91. The minor bore 93 has a diameter approximately one-third the diameter of the major bore 92; the major bore 92 corresponds in size and shape to the major bore 81 of the UDAC 72, and the minor bore 93 corresponds in size and shape to the minor bore 82 of the UDAC 72. Both of the major and minor bores 92 and 93 provide a pathway for movement of fluid into and out of the UDAC 72, depending on the selected mix or dispense function of the dispenser 10.

Two cylindrical seats are formed into a face 98 of the base 91 opposite the post 90: a major seat 96 coaxial to and communicating with the major bore 92, and a minor seat 97 coaxial to and communicating with the minor bore 93. A single gasket 99 is fit into both of the major and minor seats 96 and 97. The gasket 99 has a figure-eight shape with a large annulus and a small annulus and two holes, formed coaxially though the large and small annuli. The gasket 99 has a height just slightly greater than the depth of the major and minor seats 96 and 97, so that the gasket 99 protrudes slightly beyond the face 98 of the base 91. The gasket 99 is constructed from a material or combination of materials having characteristics of inertness, low permeability, durability, and compressibility, such as rubber. The lower ribbon 54 is applied over the gasket 99, is adhered to the face 98 of the LDAC 73 with a peelable bond, and is thereby sealed to the face 98 of the LDAC 73. The lower ribbon 54 completely overlies the gasket 99 with a continuous, annular seal formed between the lower ribbon 54 and the face 98 to act as a barrier to fluid migration.

The UDAC 72 and LDAC 73 form a sterile connector, identified as the DACA 63, between the diluent reservoir 12 and the tubing set 65. The UDAC 72 allows the diluent reservoir 12 to be sterilized separately from the tubing set 65 and then mated to the LDAC 73 without affecting the sterility of either the UDAC 72 or the LDAC 73. To form the DACA 62, the UDAC and LDAC 72 and 73 are aligned with each other so that the major bores 81 and 92 are aligned and the minor bores 82 and 93 are aligned, and the UDAC and LDAC 72 and 73 are compressed into each other. Four fingers 100, shown most clearly in FIG. 3, project axially from the base 91 of the LDAC 73, each terminating in an enlarged, radially inwardly-directed head. The fingers 100 couple and hold the UDAC 72 and LDAC 73 together in mating engagement and coaxial alignment. The fingers 100 are circumferentially spaced apart around the UDAC 72 and the LDAC 73, further maintaining coaxial alignment between the UDAC 72 and LDAC 73. When the UDAC 72 and the LDAC 73 are mated, the fingers 100 fit over the base 75 of the UDAC 72 and compress the UDAC 72 and LDAC 73 together. The gaskets 86 and 99 are thus also aligned and compressed toward each other, thereby defining a continuous figure-eight shaped pad of contact therebetween and sealing the UDAC 72 and the LDAC 73 to each other for leak-proof fluid communication. Between the gaskets 86 and 99 are the upper and lower ribbons 53 and 54. Because the upper and lower ribbons 53 and 54 are so thin, the drawings do not clearly show both of the structures; however, one having skill in the art will readily appreciate and understand that the upper and lower ribbons 53 and 54 are applied such that they are against each other and between the gaskets 86 and 99, respectively, thereby sealing the UDAC 72 and the LDAC 73 and allowing that seal to be removed. The upper and lower ribbons 53 and 54 extend from the DACA 63 through the interior 60 and out the left side 26. The upper and lower ribbons 53 and 54 are anchored in the DACA 63 and define occlusions of the DACA 63 at this anchor. The pull assembly 50, which includes the upper and lower ribbons 53 and 54, is suitable for being easily grasped and pulled such as by the fingers. FIG. 4 illustrates the pull assembly 50 still applied to the housing, with the upper and lower ribbons 53 and 54 still within the UDAC 72, and thus FIG. 4 shows the dispenser 10 in a storage state in which fluid may not yet flow into or out of the diluent reservoir 12. Placing the dispenser 10 into the use state requires at least removing the upper and lower ribbons 53 and 54 to join the UDAC 72 and the LDAC 73 in fluid communication. Arranging the dispenser 10 from the storage state to the use state is described in further detail above, after a discussion of the LACA 64.

Returning to FIG. 3, the drug reservoir 13 is shown nestled into the recess formed between the corner 70 of the diluent reservoir 12 and the housing 11, proximate to the right side 27. The drug reservoir 13 is generally cylindrical and is preferably a glass vial, though in other embodiments is a plastic vial and a plastic syringe. The drug reservoir 13 is open-ended, but closed with an upper drug aseptic connector 110 (hereinafter, "ULAC 110"), which is the upper portion of the LACA 64 and is aseptically coupled to a lower drug aseptic connector 111 (hereinafter "LLAC 111"). The ULAC 110 allows the drug reservoir 13 to be pre-filled and sterilized before assembly into the housing 11 and before coupling to the other structural elements and features of the dispenser 10. The drug reservoir 13 is preferably transparent or at least translucent so that a user can observe the drug therein and roughly measure the progress of the mixing of the drug as diluent is applied to and through the drug reservoir 13. In some embodiments, the drug reservoir 13 includes volume indication lines to indicate the volume of solid or solution—as the case may be depending on the state of the drug—in the drug reservoir 13. The drug reservoir 13 preferably can hold between approximately 0.1 and 2 grams of a drug. The specific drug carried in the drug reservoir 13 will depend on a case-by-case basis by prescription, but may include, for example, vancomycin. The drug is not shown in the drawing, as one having ordinary skill in the art will readily appreciate its existence and flow through the dispenser 10 during mixing and dispensing.

The drug reservoir 13 is capped with the ULAC 110, which, as seen in FIG. 3 and FIG. 4, includes an enlarged, inwardly-turned annular lip that catches on, fits over, and secures a neck of the drug reservoir 13. The LACA 64 is shown in best detail in FIG. 4. The ULAC 110 and LLAC 111 are mated to each other in compression to form a single, leakproof assembly. The ULAC 110 includes a stem 112 and a coaxial, wider, circular base 113 monolithically formed thereto. The stem 112 extends upward from the base 113 and is sized and shaped to fit snugly into the neck of the drug reservoir 13. The neck of the drug reservoir 13 is pressed fully into the ULAC 110 until the neck makes contact with the base 113, thereby forming a seal with the ULAC 110. The inwardly-turned annular lip of the ULAC 110 is outside the neck of the drug reservoir 13, so that the neck of the drug reservoir 13 is disposed between the lip and the stem 112. A major bore 114 and minor bore 115 extend through entirely the stem 112 and the base 113 and are coupled in fluid communication with the interior of the drug reservoir 13. The minor bore 115 has a diameter approximately one-third the diameter of the major bore 114. Both of the major and minor bores 114 and 115 provide a pathway for movement of fluid through the ULAC 110, such that fluid flows both into and out of both of the major and minor bores 114 and 115 depending on the selected mix or dispense function of the dispenser 10 at the time.

Two cylindrical seats are formed into a face 118 of the base 113 opposite the stem 112: a major seat 116 coaxial to and communicating with the major bore 114, and a minor seat 117 coaxial to and communicating with the minor bore 115. A single gasket 120 is fit into both of the major and minor seats 116 and 117; the gasket 120 has a figure-eight shape with a large annulus and a small annulus and two holes formed coaxially though the large and small annuli.

The gasket 120 has a height just slightly greater than the depth of the major and minor bores 114 and 115, so that the gasket 120 protrudes slightly beyond the face 118 of the base 113. The gasket 120 is constructed from a material or combination of materials having characteristics of inertness, low permeability, durability, and compressibility, such as rubber. The upper ribbon 56 is applied over the gasket 120, is adhered to the face 118 of the ULAC 110 with a peelable bond, and is thereby sealed to the face 118 of the ULAC 110. The upper ribbon 56 completely overlies the gasket 120 with a continuous, annular seal formed between the upper ribbon 56 and the face 118 to act as a barrier to fluid migration.

The LLAC 110 is similar to the LDAC 72 in the LACA 63. The LLAC 110 includes a post 121 and a wide, circular base 122 extending coaxially therefrom. A major bore 123 extends vertically through the base 121 and turns laterally, reducing in diameter in the post 122 before extending horizontally out of the post 122 as a barbed coupling 125. A minor bore 124 extends vertically through both the base 121 and the post 122 and terminates as a barbed coupling 126 pointing down. The major and minor bores 123 and 124 are entirely separated by an internal wall in the post 121 and the base 122. The minor bore 124 has a diameter approximately one-third the diameter of the major bore 123; the major bore 123 corresponds in size and shape to the major bore 114 of the ULAC 110, and the minor bore 124 corresponds in size and shape to the minor bore 115 of the ULAC 110. Both of the major and minor bores 123 and 124 provide a pathway for movement of fluid into and out of the ULAC 110, depending on the selected mix or dispense function of the dispenser 10.

Two cylindrical seats are formed into a face 129 of the base 122 opposite the post 121: a major seat 127 coaxial to and communicating with the major bore 123, and a minor seat 128 coaxial to and communicating with the minor bore 124. A single gasket 130 is fit into both of the major and minor seats 127 and 128. The gasket 130 has a figure-eight shape with a large annulus and a small annulus and two holes, formed coaxially though the large and small annuli. The gasket 130 has a height just slightly greater than the depth of the major and minor seats 127 and 128, so that the gasket 130 protrudes slightly beyond the face 129 of the base 122. The gasket 130 is constructed from a material or combination of materials having characteristics of inertness, low permeability, durability, and compressibility, such as rubber. The lower ribbon 57 is applied over the gasket 130, is adhered to the face 129 of the LLAC 111 with a peeable bond, and is thereby sealed to the face 129 of the LLAC 111. The lower ribbon 57 completely overlies the gasket 130 with a continuous, annular seal formed between the lower ribbon 57 and the face 129 to act as a barrier to fluid migration.

The ULAC 110 and LLAC 111 form a sterile connector, identified as the LACA 64, between the drug reservoir 13 and the tubing set 65. The ULAC 110 allows the drug reservoir 13 to be sterilized separately from the tubing set 65 and then mated to the LLAC 111 without affecting the sterility of either the ULAC 110 or the LLAC 111. To form the LACA 64, the ULAC and LLAC 110 and 111 are aligned with each other so that the major bores 114 and 123 are aligned and the minor bores 115 and 124 are aligned, and the ULAC and LLAC 110 and 111 are compressed into each other. Four fingers 101, shown most clearly in FIG. 3, project axially from the base 122 of the LLAC 111, each terminating in an enlarged, radially inwardly-directed head. The fingers 101 couple and hold the ULAC 110 and LLAC 111 together in mating engagement and coaxial alignment. The fingers 101 are circumferentially spaced apart around the ULAC 110 and the LLAC 111, further maintaining coaxial alignment between the ULAC 110 and the LLAC 111. When the ULAC 110 and the LLAC 111 are mated, the fingers 101 fit over the base 113 of the ULAC 110 and compress the ULAC 110 and LLAC 111 together. The gaskets 120 and 130 are aligned and compressed toward each other, thereby defining a continuous figure-eight shaped pad of contact therebetween and sealing the ULAC 110 and the LLAC 111 to each other for leak-proof fluid communication. Between the gaskets 86 and 130 are the upper and lower ribbons 56 and 57. Because the upper and lower ribbons 56 and 57 are so thin, the drawings do not clearly show both of the structures; however, one having skill in the art will readily appreciate and understand that the upper and lower ribbons 56 and 57 are applied against each other and between the gaskets 120 and 130, respectively, thereby sealing the ULAC 110 and the LLAC 111 and allowing that seal to be removed. The upper and lower ribbons 56 and 57 extend from the LACA 64 through the interior 60 and out the back 23. The upper and lower ribbons 56 and 57 are anchored in the LACA 64 and define occlusions of the LACA 64 at this anchor. The pull assembly 51, which includes the upper and lower ribbons 56 and 57, is suitable for being easily grasped and pulled such as by the fingers. FIG. 4 illustrates the pull assembly 51 still applied to the housing 11, with the upper and lower ribbons 56 and 57 still within the ULAC 110, and thus FIG. 4 shows the dispenser 10 in a storage state in which fluid may not yet flow into or out of the drug reservoir 13 to mix with or dispense the drug. Placing the dispenser 10 into the use state requires at least removing the upper and lower ribbons 56 and 57 from LACA 64 to join the ULAC 110 and the LLAC 111 in fluid communication, and, as discussed above, also requires removing the upper and lower ribbons 53 and 54 from DACA 63 to join the UDAC 72 and the LDAC 73 in fluid communication.

Still referring to FIG. 4, energy storage means, or a battery supply 131, is also carried in the interior 60 of the housing 11 to power the dispenser 10. The battery supply 131 is preferably located proximate to the left side 26, so that it is disposed in close relation to the pull assembly 50. A switch assembly 132 is proximate the battery supply 131 and connected to the PCB 40. The switch assembly 132 is disposed above the pull assembly 50, opposite the battery supply 131, and is useful for maintaining the dispenser 10 in the storage state and later easily moving it into the use state. The switch assembly 132 includes upper electrical contacts 133 interrupted from the battery supply 131 by the pull assembly 50 threaded therebetween. The pull assembly 50 is constructed of a non-conductive material, and so when the pull assembly 50 is interposed between the upper electrical contacts and the battery supply 131, electrical communication between the upper electrical contacts 133 and the battery supply 131 is prevented and the switch assembly 131 is open. When the pull assembly 50 is removed from the switch assembly 132, such as would occur when a user grasps and pulls the pull assembly 50 to energize the dispenser 10 from the storage state to the use state, the upper electrical contacts 133 and the battery supply 131 are brought into contact with each other and are coupled in electrical communication. Coupling the upper electrical contacts 133 to the battery supply 131 in electrical communication closes the switch assembly 132 and energizes the dispenser 10 by providing power to the PCB 40.

Returning to FIG. 3, but with reference also still to FIG. 4, the tubing set 65 is shown. The tubing set 65 extends between and joins in fluid communication the diluent reservoir 12, the drug reservoir 13, and the administration line 14. The tubing set 65 includes an upper tube 140 extending directly between the diluent reservoir 12 and the drug reservoir 13, a down tube 141 extending downwardly from the diluent reservoir to a tee 142, a pump tube 143 extending between the tee 142 and the drug reservoir 13 and routed through a pump assembly 150, and an exit tube 144 which extends from the tee 142 to a coupling at the bottom 25 of the housing 11 coupled to the administration line 14 outside the housing 11. The tubing set 65 is sterilized. Each of the tubes 140, 141, 143, and 144 are constructed of a material or combination of materials having characteristics of flexibility, fluid impermeability, and compressibility, such as polyvinylchloride, polyurethane, silicone, or the like. The upper tube 140 is press fit onto the barbed coupling 94 of the LDAC 73 and the barbed coupling 125 of the LLAC 111. The diluent tube 141 is press fit onto the barbed coupling 95 of the LDAC 73 and the pump tube 143 is press fit onto the barbed coupling 126 of the LLAC 111.

The down tube 141, the pump tube 142, and the exit tube 144 are a single piece, formed monolithically to each other and joined at the tee 142. Within the tee 142 is a check valve that controls the direction of flow within the tubing set 65. The pump assembly 150 operates in either a mix (through reconstitution or dilution) state or a dispense state. When the pump assembly 150 is in the mix state, diluent flows out of the diluent reservoir 12 down the diluent tube 141, through the tee 142, through the pump tube 143, and into the drug reservoir 13, before returning to the diluent reservoir 12 for continued mixing and further cycling. Thus, when the pump assembly 150 is operating in the mix state, the check valve within the tee 142 allows fluid to move only from the diluent tube 141 to the pump tube 143. Then, when the pump assembly 150 is placed in the dispense state, fluid flows out of the diluent reservoir 12 directly to the drug reservoir 13 through the upper tube 140, then down the pump tube 143, through the tee 142, and down the exit tube 144 to the administration line 14. Thus, in the dispense state of the pump assembly 150, fluid is prevented from returning to the diluent reservoir 12; the tee 142 allows fluid to move only from the pump tube 143 to the exit tube 144.

Figure 5:
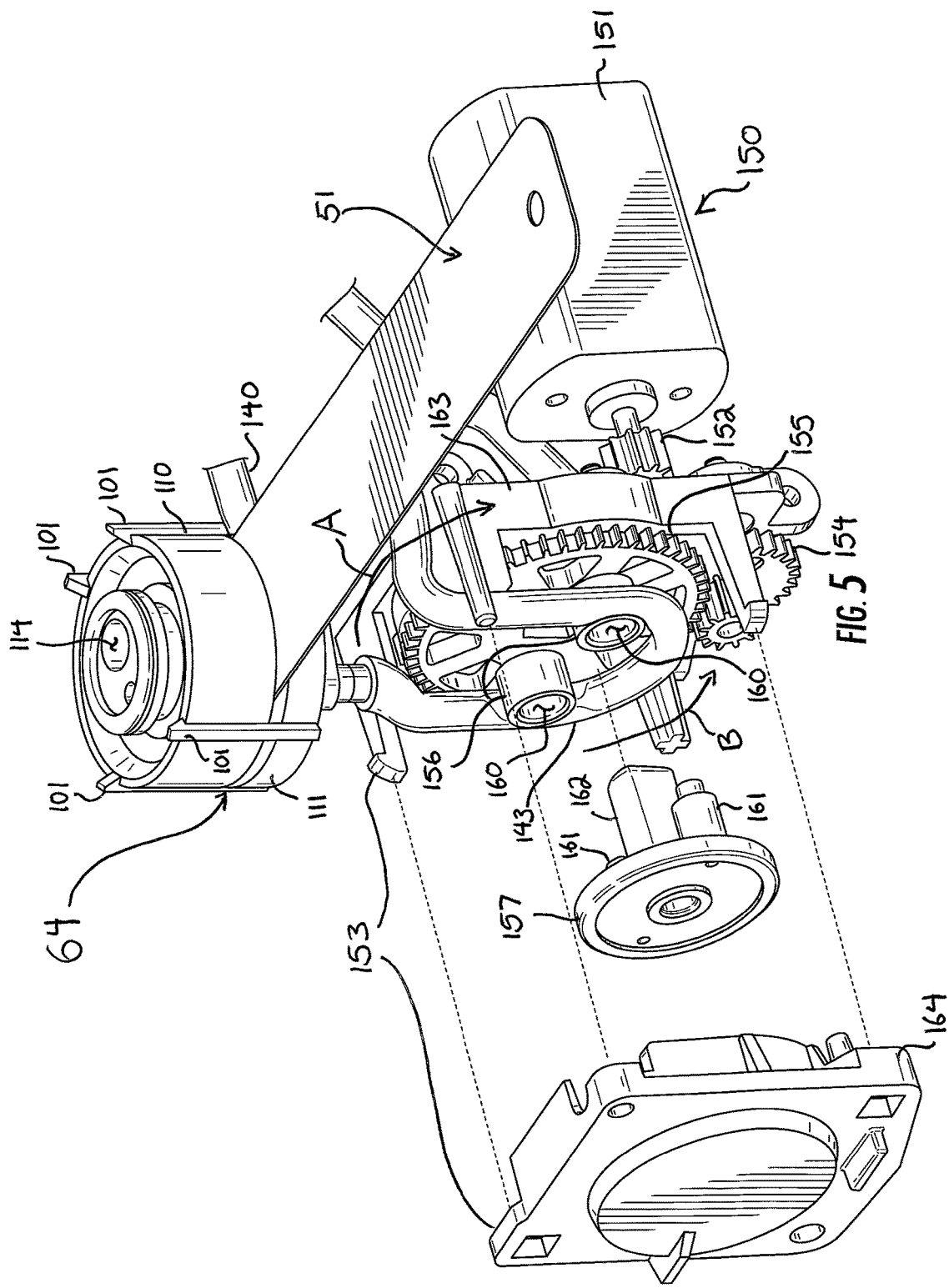
FIG. 5 is an isolated, exploded view of the pump assembly and portions of the tubing set.
Figure 7:
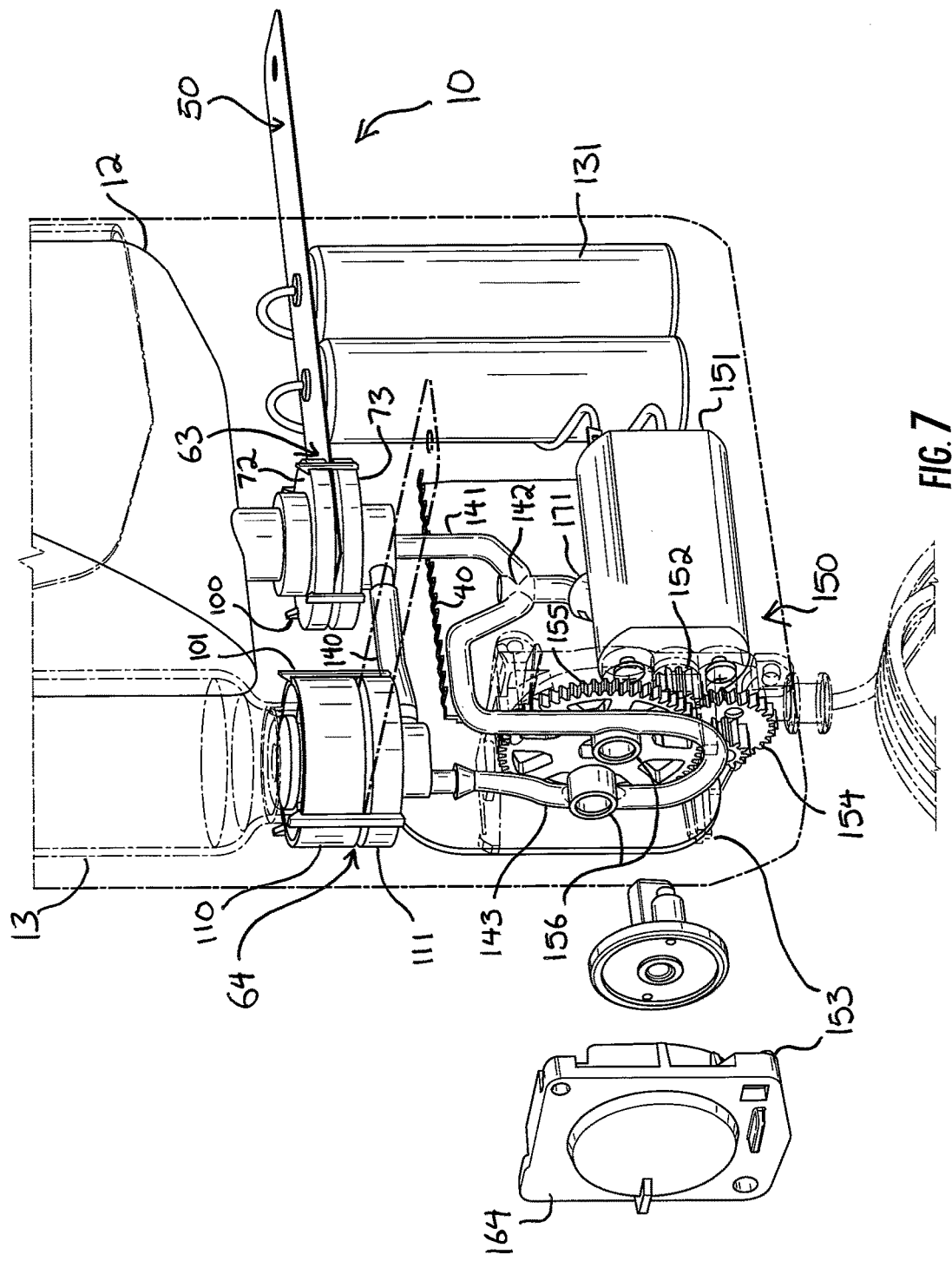
FIG. 7 is a rear perspective view of the unified drug mixer and dispenser of FIG. 1, with the housing hidden and the pump assembly partially exploded.

The pump assembly 150 draws diluent from the diluent reservoir 12 to mix with and reconstitute or dilute the drug in the drug reservoir 13, to form a liquid medicament. As the terms are used here, diluent will refer to both pure diluent and diluent that has begun to be mixed with the drug, and liquid medicament is diluent that has been fully mixed with the reconstituted or diluted drug to the appropriate concentration for dispensing to the patient. FIGS. 5, 6, and 7 show the pump assembly 150 best. FIG. 5 illustrates the pump assembly 150, the LACA 64, the pull assembly 51, and the pump tube 143 routed through the pump assembly 51, isolated from the housing 11 and the other components in the housing 11.

The pump assembly 150 includes a motor 151 with a small spur gear 152 secured on its shaft for rotation. The motor 151 is a DC or step motor powered by the battery supply 131 and controlled by a MOSFET or other logic on the PCB 40. The spur gear 152 is sufficiently long to extend into a box 153 holding a reduction gear 154 and a main gear 155; the spur gear 152 is meshingly engaged to the reduction gear 154, and the reduction gear 154 in turn is meshingly engaged to the main gear 155. Two rollers 156 are held against the main gear 155, and a cap 157 fits over the rollers 156 and into the main gear 155 to hold the rollers 156 with and against the main gear 155 during rotation thereof. The rollers 156 each include axial bores 160 that correspond to through-holes in the main gear 155, and the cap 157 includes two posts 161 that extend through the bores 160 and the through-holes to lock into the main gear 155, thereby securing the rollers 156 in corresponding rotation with the main gear 155. The cap 157 further includes a square-shaped plug 162 that fits into a corresponding socket in the main gear 155. FIGS. 5-7 show an embodiment in which there are two rollers 156, but there may be three or four rollers 156 in other embodiments. The rollers 156 extend toward the right side 27 of the housing 11 from the main gear 155 parallel to the axis of rotation of the main gear 155.

The box 153 includes a left panel 163 and a right panel 164 mated to each other. Referring briefly to just FIG. 6, the right panel 164 includes an arcuate, roughly semi-circular internal wall 165. The pump tube 143 is routed through the pump assembly 150 inside the box 153 and along an inside face 166 of the internal wall 165. The tube set 143 is disposed between the internal wall 165 and the rollers 156, and the rollers 156 rotate to impinge and compress the pump tube 143 against the inside face 166 of the internal wall 165 to occlude the pump tube 143. When the main gear 155 is rotated so that the two rollers 156 compress the pump tube 143, diluent or liquid medicament—depending on the operational state of the dispenser 10—is trapped in the pump tube 143 between the two rollers 156 so that a certain volume of diluent or liquid medicament is controllably withheld in the tube set 143 and then released into the rest of the tubing set 65 when the leading roller stops compressing the pump tube 143. As will be described later, the motor 151 rotates the main gear 155 in both directions, depending on the operational state of the dispenser 10, so that either of the rollers 156 may be leading rollers 156.

Referring to FIGS. 4 and 7 now, the pump tube 143 extends out of the pump assembly 150 to the tee 142, from which the exit tube 144 depends down the bottom 25 of the housing 11. Before the tubing set 65 exits the housing 11, however, it passes a force-sensing resistor 170 mounted to the PCB 40. A constricting channel 171 is carried over the tubing set 65 opposite the force-sensing resistor 170. The constricting channel 171 is a rigid, elongate, semi-cylindrical structure secured to the PCB 40. The constricting channel 171 has an inner diameter equal to the outer diameter of the tubing set 65 and prevents the tubing set 65 from swelling or expanding radially. The force-sensing resistor 170 is disposed on the PCB 40 at the constricting channel 171, so that the tubing set 65 is in direct contact with the force-sensing resistor 170 when routed through the constricting channel 171. The force-sensing resistor 170 is coupled in electrical communication to logic carried on the PCB 40. The force-sensing resistor 170 measures a compressive force acting on it, and with the logic on the PCB 40, determines the extent of swelling or radial expansion in the tubing set 65, and, correspondingly, a correlated internal pressure of the tubing set 65. In some embodiments, the tubing set 65 has a thin sidewall, allowing for more precise measurements of force.

The exit tube 144 bends downward and into a strain-relief coupling 180 fitted into the bottom 25 of the housing 11 and to which the administration line 14 is coupled. The administration line 14 is a long, flexible, tubing terminating in the coupling 15, which is a luer fitting or the like, and is capped to maintain the sterility of the administration line 14.

A medical professional preparing the dispenser 10 for use with a patient obtains the dispenser 10 in preferably a packaged state. The dispenser 10, including the housing 11, the components within the housing 11, and the administration line 14, are contained within the packaging. Such packaging need not necessarily be a sterilized packaging, given that the fluid communication path 62 was previously sterilized before assembly and will thus be sterile upon the opening of the packaging by the medical professional. The fluid communication path 62, being composed of the diluent reservoir 12, the drug reservoir 13, the DACA 63, the LACA 64, the tubing set 65, and the administration line 14, is sterilized in several separate steps.

In one step, the diluent reservoir 12 is filled with the diluent and then applied with the UDAC 72. The upper ribbon 53 is already sealed to the face 85 of the UDAC 72. The entire assembly of the diluent reservoir 12, the UDAC 72, and the upper ribbon 53 is then sterilized with conventional sterilization methods. This places the diluent reservoir 12 in a long-term, sterilized state. In an embodiment of another step, the drug reservoir 13 is filled with a liquid drug, which is then lyophilized (freeze-dried) into a powder according to conventional methods. In an alternate embodiment of the other step, the drug reservoir 13 is filled with a powdered drug. In another embodiment of the other step, the drug reservoir 13 is filled with a crystalline drug, or the drug reservoir 13 is filled with a liquid drug which is then subjected to a conventional crystallization process. In yet another embodiment of the other step, the drug reservoir 13 is filled with a solution state drug and maintained in that solution state. Regardless of the method of filling the drug reservoir 13 with the drug, the ULAC 110, with the upper ribbon 56 already sealed to the face 118, is applied to the drug reservoir 13 and sealed thereto with an irreversible press-fit engagement; the neck of the drug reservoir 13 is pressed fully into the ULAC 110 until the neck makes contact with the base 113, forming a seal with the ULAC 110. This places the drug reservoir 13 in a long-term, sterilized state. In another step, the tubing set 65 is capped with the LDAC 73 (the down tube 141 is press fit onto the barbed coupling 95 and the upper tube 140 is press fit onto the barbed coupling 94), the LLAC 111 (the pump tube 143 is press fit onto the barbed coupling 126 and the upper tube 140 is press fit onto the barbed coupling 125), and the strain-relief coupling 180, and the assembly is then Gamma- or ETO-sterilized. The lower ribbons 54 and 57 are applied to the LDAC 73 and LLAC 111, respectively, before the LDAC 73 and LLAC 11 are coupled to the tubing set 65. The administration line 14 is similarly sterilized.

Each of these components being sterilized and now defining a closed system, they are then assembled into the housing 11. The housing 11 already includes the pump assembly 150, the PCB 40, and the battery supply 131 applied therein. There are two methods of assembling the tubing set 65 and administration line 14 to the housing 11, depending on the construction of the housing 11. When the housing 11 is constructed from two or more pieces, and a seam runs along the bottom of the housing, the tubing set 65 and administration line 14 are coupled to each other with a strain-relief coupling 160 and sterilized. The assembly of the tubing set 65, the administration line 14, and the strain-relief coupling 180 are then placed into a piece of the housing 11, and an opposing piece of the housing 11 is applied thereto, with the strain-relief coupling 180 fit into a hole formed between the two pieces of the housing 11 at the bottom 25 of the housing 11. Alternatively, when the housing 11 is constructed from a single piece of material, and includes a hole at the bottom 25, the tubing set 65 is placed into the housing and the strain-relief coupling 180 is fit into the hole at the bottom 25 of the housing 11. The administration line 14 is then coupled to the strain-relief coupling 180 and sterilized.

The drug reservoir 13 is then placed into the housing 11, and the ULAC 110 is mated against the LLC 111 so that the upper and lower ribbons 56 and 57 are against each other to form the pull assembly 51. The pull assembly 51 is threaded through the slit 55 in the back 23 of the housing 11. Finally, the diluent reservoir 12 is placed into the housing 11 atop the drug reservoir 13, and the UDAC 72 and LDAC 73 are mated against each other. The upper and lower ribbons 53 and 54 are against each to form the pull assembly 50 which is threaded through the slit 52 on the left side 26 of the housing 11. The pull assembly 50 is also passed between the battery supply 131 and the switch assembly 132 to prevent electrical contact therebetween. Assembled in this manner, the sterility of the fluid communication path 62 is maintained and protected. The dispenser 10 is then ready for shipping through distribution to medical professionals in this storage state.

When a medical professional receives the dispenser 10, it is initially in the storage state and is thus not capable of dispensing liquid medicament. The medical professional prepares a dispenser 10 for use first by selecting the appropriate dispenser 10 containing the medicament needed. For example, if vancomycin must be administered to the patient, the medical professional obtains a dispenser 10 containing lyophilized vancomycin. It is noted here that the dispenser 10 is effective at delivering a variety of drug products, including drugs which are administered at fixed rate, at a variable rate, based on a patient weight, a patient surface area, or on some other basis.

Non-limiting examples of solid state drugs, such as dried, powdered, lyophilized powdered, or crystallized drugs, for use in the dispenser 10 include, but are not limited to: Vancomycin, Cefazolin, Cefoxitin, Ceftriaxone, Linezolid, Ampicillin, Solu-cortef®, Pipracil®, Azithromycin, Cefepime, Veftazidime, Cefuroxime, Oxacillin, Meropenem, Cefotaxime, Gentamicin, Tobramycin, Cimetidine, Bexxar®, Emend®, Campath®, Flagyl®, Levaquin®, Unasyn®, Zosyn®, Cefoxitin, Primaxin®, Ampicillin, Clindamycin, Cefepime, Caspofungin, Cefotetan, Meropenem, Tobramycin, Primaxin, Quinupristin and Dalfopristin (Synercid®), Rifampin, Cladribine, Thiotepa, Taliglucerase Alfa (Elelyso®), Velaglucerase Alfa (Vpriv®), IVIG, Hemin, Trastuzumab (Herceptin®, Herclon™), Cyclophosphamide (Lyophilized cytoxan, Endoxan, Cytoxan®, Neosar®, Procytox, Revimmune™, Cycloblastin), Dacarbazine (DTIC-Dome®), Plicamycin (Mithracin™), Trimetrexate, Mitomycin, Sargramostim (Leukine®), Bendamustine, Bortezomib (Velcade®), Gemtuzumab Ozogamicin (Mylotarg®), Fludarabine, Gemcitabine, Carmustine, Dacarbazine, Dexrazoxane, Doxorubicin, Etoposide, Ifosfamide, and Pembrolizumab (Keytruda®) (anti-PD1).

Non-limiting examples of solution state drugs for use in the dispenser include, but are not limited to: Tysabri®, Actemra®, Dolasetron, Labetolol, Soliris®, Bleomycin™, Arzerra®, Dobutamine, Bevacizumab (Avastin®), Filgrastim (Neupogen®), Panitumumab (Vectibix®), Dacarbazine (DTIC-Dome®), Docetaxel, Mitoxantrone, Sargramostim (Leukine®), Teniposide (Vumon®), Rituximab (Rituxan®), Cetuximab (Erbitux®), Gemtuzumab Ozogamicin (Mylotarg®), Irinotecan, Oxaliplatin, Paclitaxel, Topotecan, Vinorelbine, Carboplatin, Cisplatin, Dacarbazine, Doxorubicin, Idarubicin, Oxaliplatin, Nivolumab (Opdivo®) (anti-PD1), docetaxel (DOCEFREZ®) (Taxotere®), paclitaxel (TAXOL®), ferumoxytol (Ferheme®), dexmedetomedine (Precedex®), and all taxanes (cabazitaxel, Paclitaxel®, Docetaxel®) (diterpenes produced by the plants of the genus *Taxus* (yews) featuring a taxadiene core).

Non-limiting examples of other drugs for use in the dispenser 10 include, but are not limited to: Pidilizumab (anti-PD-1), ipilimumab (anti-CTLA-4), anti-PD1 (anti-programmed death receptor-1), anti-PD-L1 (anti-programmed death receptor-1 Ligand), durvalumab (anti-PD-L1), avelumab (anti-PD-L1), atezolizumab (anti-PD-L1), anti-OX40 (anti-CD134 MoAb), anti-4-1BB (anti-CD137 monoclonal antibody) (urelumab), anti-GITR (anti-human glucocorticoid-induced tumor necrosis factor receptor (GITR) agonistic monoclonal antibody (MoAb)), anti-TIM2 (T cell immunoglobulin and mucin domain containing 2 Antibody), anti-LAG3 (monoclonal antibody directed against the inhibitor receptor lymphocyte activation gene-3 (LAG-3™)), anti-TNFRSF25 (mAb that binds to Tumor Necrosis Factor (TNF) receptor superfamily member 25 (TNFRSF25)), anti-ICOS (anti-inducible costimulator (ICOS), member of the costimulatory molecule family), all light-activated drugs for tumor ablation, anti-EGFR, anti-TGFbeta, IDO and TDO inhibitors, kynurenine inhibitors and cleavage enzymes all inhibitors of the tryptophan metabolic pathway, anti-phosphatidylserine antibody-drug conjugates containing a tumor-targeting moiety and a cytotoxic moiety, bi-specific antibodies or proteins containing targets present on tumor cells and T cells, or on tumor cells and B cells, or on tumor cells and other lymphocytes, or on T cells and antigen-presenting cells, anti-VEGF, BTK inhibitors, RAS inhibitors, MET inhibitors, and any combinations of two or more of the above agents.

After selecting the appropriate dispenser 10, the medical professional removes the dispenser 10 from its packaging and arranges the dispenser 10 for use, such as by hanging from the hole 21 off of a stand proximate to the patient. The cap on the coupling 15 is removed and connected to a catheter already secured to the patient. In this manner, the fluid communication path 62 is coupled to the catheter on the patient with minimal opportunity for contamination. The medical professional then begins operating the dispenser 10.

The dispenser 10 is shipped in the storage state. In the storage state, the fluid communication path 62 is sterile and connected to the diluent reservoir 12, to the drug reservoir 13, and through the pump assembly 150, but is occluded by the upper and lower ribbons 51 and 52 on the DACA 3 and the upper and lower ribbons 56 and 57 on the LACA 64. Further, in the storage state, the dispenser 10 is not energized: no power is provided to the PCB 40 or the motor 151, and the PCB 40 and the motor 151 are each electrically isolated from the battery supply 131. To operate the dispenser 10 in the use state, the medical professional must first both energize the dispenser 10 and remove these occlusions.

Energizing the device is accomplished by pulling and removing the pull assembly 50, which removes the occlusion formed by the upper and lower ribbons 53 and 54 in the DACA 63. As the pull assembly 50 is drawn out of the housing 11, the upper and lower ribbons 53 and 54 are peeled off of the faces 85 and 98, and the gaskets 86 and 99 come into direct and sealing contact with each other, still biased into compression with each other. With the UDAC 72 and LDAC 73 maintained in coaxial alignment by the fingers 100 and the gaskets 86 and 99 thus also maintained in coaxial alignment, the major bores 81 and 92 and the minor bores 82 and 93 in the UDAC 72 and LDAC 73 are coupled in respective fluid communication with each other. At approximately the same time, the pull assembly 51 is pulled and removed from the housing 11, which removes the occlusion formed by the upper and lower ribbons 56 and 57 in the LACA 64. As the pull assembly 51 is drawn out of the housing 11, the upper and lower ribbons 56 and 57 are peeled off of the faces 118 and 129, and the gaskets 120 and 130 come into direct and sealing contact with each other, still biased into compression with each other. With the ULAC 110 and LLAC 111 maintained in coaxial alignment by the fingers 101, and the gaskets 120 and 130 thus also maintained in coaxial alignment, the major bores 114 and 123 and the minor bores 115 and 124 of the ULAC 110 and LLAC 111 are coupled in respective fluid communication with each other.

Further, with the pull assembly 50 removed from the housing 11, the battery supply 131 and the switch assembly are coupled in electrical contact, so that power is supplied to the PCB 40 and the motor 151 from the battery supply 131. The dispenser 10 is now arranged in the use state and ready for operation by the medical professional. There are two types of use states of the dispenser 10: a mix state and a dispense state. The dispenser 10 is programmed to not enter the dispense state until the mix state has been concluded. Thus, the medical professional must first place the dispenser 10 into the mix state.

Depending on the drug contained with the dispenser 10, the medical professional will operate the setting and navigation buttons 34-36 differently. Each time one of the buttons 34-36 is depressed, the dispenser 10 produces a tactile, haptic, or audible feedback to the medical professional to provide additional confirmation that a button has been pressed. A small, eccentric motor and speaker assembly is mounted in the interior 60 of the housing 11 and coupled to the battery supply 131 and the PCB 40. In response to one of the buttons 34-36 being depressed, the eccentric motor rotates, or the speaker emits a sound, such as a beep. When the medical professional has selected the correct setting, the medical professional will depress the mix button 41. Depression of the mix button 41 places the dispenser in the mix state, and initiates reconstitution, mixing, or dilution of the drug, depending on whether the drug is a solid state or solution state drug. Logic on the PCB 40 initiates operation of the motor 151 to rotate the spur gear 152, causing the main gear 155 to rotate in the direction A as indicated in FIG. 5 and FIG. 6. The pump assembly 150 thus pulls diluent from the diluent reservoir 12, down the diluent tube 141, through the tee 142, through the pump tube 143, and into the drug reservoir 13 before returning to the diluent reservoir 12 along the upper tube 140 for continued mixing and further cycling. Mix times vary by drug, but typically range between ten seconds and five minutes. In some cases, mixing requires the medical professional to gently swirl or move the dispenser 10 to agitate the fluid and promote mixing. The main gear 155 rotates until the drug is fully reconstituted or diluted, evenly distributed through the diluent, and the resulting liquid medicament is homogenous. An alert, such as a blinking light or an auditory beep, indicates to the medical professional that the liquid medicament is ready for dispensation to the patient. The display 33 shows the menus and settings through which the medical professional navigates.

To dispense the liquid medicament to the patient, the medical professional depresses the dispense button 42. Depression of the dispense button 42 places the dispenser 10 in the dispense state. The PCB 40 initiates operation of the motor 151 to rotate the spur gear 152 in a direction opposite to the previous direction. This causes the main gear 155 to rotate in the direction B indicated in FIG. 5 and FIG. 6. The pump assembly 150 now pulls liquid medicament out of the diluent reservoir 12 through the upper tube 140, into the drug reservoir 13, down through the pump tube 143 routed through the pump assembly 150, through the tee 142, and down the exit tube 144 to the administration line 14. The motor 151 rotates at a speed determined by the logic on the PCB 40 based on the parameters selected by the medical professional and shown in the display 33. The rotational speed of the main gear 155 is monitored by an optical assembly. The optical assembly includes a transmitter emitting an optical signal, such as a light or laser, and a receiver disposed on opposed sides of the main gear 155, such as in the left and right panels 163 and 164. The main gear 155 is slotted with regular, pie-shaped holes, so that the main gear 155 periodically and regularly blocks and allows the optical signal. When the main gear 155 interposed between the transmitter and receiver, the optical signal is blocked and the receiver records nothing. When one of the holes on the main gear 155 is disposed between the transmitter and the receiver, however, the optical signal is received and the receiver records such receipt. Hence, the optical assembly records a series of interspersed, sequential receipts of the optical signal, and because the width of the holes is known, logic on the PCB 40 determines the rotational speed of the main gear 155 from the number of successful optical receipts and the duration of such receipts. This, in turn, allows the logic on the PCB 40 to determine the rate at which diluent is being supplied to the drug reservoir 13 (during the mix state) and the rate at which medicament is supplied to the patient (during the dispense state). Dispensation of the liquid medicament is paused or stopped by depressing the dispense button 42 a second, and is then resumed by depressing it again.

A preferred embodiment is fully and clearly described above so as to enable one having skill in the art to understand, make, and use the same. Those skilled in the art will recognize that modifications may be made to the described embodiment without departing from the spirit of the invention. To the extent that such modifications do not depart from the spirit of the invention, they are intended to be included within the scope thereof.

The invention claimed is:

1. An aseptic connector assembly comprising:
   an upper aseptic connector in which an upper gasket is received, an opposed lower aseptic connector in which a lower gasket is received, and occlusions acting as barriers to fluid migration between the upper and lower aseptic connectors;
   the occlusions are removable from between the upper and lower gaskets to change the aseptic connector assembly from a storage state to a use state;
   in the storage state of the aseptic connector assembly, the upper and lower aseptic connectors are coupled and compressed together, thereby compressing the upper and lower gaskets against each other with the occlusions therebetween, and the occlusions occlude the aseptic connector assembly preventing fluid migration through the aseptic connector assembly; and
   in the use state of the aseptic connector assembly, the upper and lower aseptic connectors are coupled and compressed together, thereby compressing the upper and lower gaskets against each other, and the occlusions are removed from the aseptic connector assembly, thereby bringing the upper and lower gaskets into direct and sealing contact with each other, defining a pathway for fluid migration through the aseptic connector assembly;
   wherein, as the aseptic connector assembly is moved from the storage state to the use state, the upper and lower aseptic connectors remain coupled to each other and are maintained in coaxial alignment with each other.

2. The aseptic connector assembly of claim 1, wherein the occlusions comprise upper and lower ribbons over the upper and lower gaskets, respectively.

3. The aseptic connector assembly of claim 2, further comprising:
   a face of the upper aseptic connector in which the upper gasket is received;
   a face of the lower aseptic connector in which the lower gasket is received; and
   the upper and lower ribbons are adhered to the respective faces of the upper and lower aseptic connectors.

4. The aseptic connector assembly of claim 2, wherein the upper and lower ribbons are against each other between the upper and lower aseptic connectors.

5. The aseptic connector assembly of claim 1, wherein removal of the occlusions is irreversible.

6. The aseptic connector assembly of claim 1, further comprising fingers formed on one of the upper and lower aseptic connectors, the fingers coupling and holding the upper and lower aseptic connectors together in compressive, mating engagement.

7. The aseptic connector assembly of claim 1, wherein the occlusions are encased within the aseptic connector assembly.

8. The aseptic connector assembly of claim 7, further comprising:
   a pull assembly coupled to the occlusions, the pull assembly extending outside of the aseptic connector assembly; and
   removal of the pull assembly removes the occlusions from the aseptic connector assembly.

9. An aseptic connector assembly comprising:
   an upper aseptic connector and a lower aseptic connector, each including:
   a base, and a stem extending from the base;
   a bore formed entirely through the base and stem, providing a pathway for fluid migration through the base and stem;
   a seat formed in a face of the base opposite the stem, and a gasket fit into the seat; and
   an occlusion sealing the bore and acting as a barrier to fluid migration through the base and stem;
   wherein the upper and lower aseptic connectors are coupled to each other.

10. The aseptic connector assembly of claim 9, wherein each occlusion comprises a ribbon over the bore.

11. The aseptic connector assembly of claim 10, wherein each ribbon is adhered to the face of the respective aseptic connector.

12. The aseptic connector assembly of claim 10, wherein the ribbons of the upper and lower aseptic connectors are against each other between the upper and lower aseptic connectors.

13. The aseptic connector assembly of claim 9, wherein the occlusions are irreversibly removable.

14. The aseptic connector assembly of claim 9, further comprising fingers formed on one of the upper and lower aseptic connectors, the fingers coupling and holding the upper and lower aseptic connectors together in compressive, mating engagement.

15. The aseptic connector assembly of claim 9, wherein each of the occlusions is encased within the aseptic connector assembly.

16. The aseptic connector assembly of claim 15, further comprising:

a pull assembly coupled to each of the occlusions, the pull assembly extending outside of the aseptic connector assembly; and removal of the pull assembly removes each of the occlusions from the aseptic connector assembly.

17. The aseptic connector assembly of claim 9, wherein the bore in each of the upper and lower aseptic connectors comprises at least one bore.

18. An aseptic connector assembly comprising:

an upper aseptic connector and a lower aseptic connector, each including:

a base, and a stem extending from the base;

a bore formed entirely through the base and stem, providing a pathway for fluid migration through the base and stem; and an occlusion sealing the bore and acting as a barrier to fluid migration at the base;

a pull assembly coupled to the occlusions;

wherein, in a storage state of the aseptic connector assembly, the occlusions are entirely encased within the aseptic connector assembly and occlude a fluid communication path through the aseptic connector assembly; and removal of the pull assembly removes the occlusions and opens the fluid communication path through the aseptic connector assembly, thereby arranging the aseptic connector assembly into a use state.

19. The aseptic connector assembly of claim 18, wherein each occlusion comprises a ribbon over the bore.

20. The aseptic connector assembly of claim 19, further comprising, for each of the upper and lower aseptic connectors, a face of the base opposite the stem, wherein the ribbon is adhered to the face.

21. The aseptic connector assembly of claim 19, wherein the ribbons of the upper and lower aseptic connectors are against each other between the upper and lower aseptic connectors.

22. The aseptic connector assembly of claim 18, wherein removal of the occlusions is irreversible.

23. The aseptic connector assembly of claim 18, further comprising fingers formed on one of the upper and lower aseptic connectors, the fingers coupling and holding the upper and lower aseptic connectors together in compressive, mating engagement.

24. The aseptic connector assembly of claim 18, wherein the pull assembly extends outside of the aseptic connector assembly.

25. The aseptic connector assembly of claim 18, wherein the bore in each of the upper and lower aseptic connectors comprises at least one bore.

* * * * *